United States Patent [19]

Moore et al.

[11] Patent Number: 5,081,250

[45] Date of Patent: Jan. 14, 1992

[54] REGIOSPECIFIC CARBONYLATION PROCESS FOR MAKING ACYL COMPOUNDS FROM AROMATIC HETEROCYCLES AND OLEFINS

[75] Inventors: Eric J. Moore, Carol Stream; Wayne R. Pretzer, Wheaton, both of Ill.

[73] Assignee: Amoco Corporation, Chicago, Ill.

[21] Appl. No.: 394,008

[22] Filed: Aug. 15, 1989

Related U.S. Application Data

[63] Continuation-in-part of Ser. No. 170,839, Mar. 21, 1988, abandoned.

[51] Int. Cl.$^5$ ............... C07D 213/46; C07D 213/22; C07D 237/06; C07D 241/10
[52] U.S. Cl. ...................... 546/340; 546/88; 546/168; 546/257; 544/224; 544/406
[58] Field of Search ............... 546/344, 88, 168, 262, 546/340, 257; 549/64; 544/406, 224

[56] References Cited

U.S. PATENT DOCUMENTS 3,840,547 10/1974 Mendelson .................... 546/340
3,979,400 9/1976 Rieger et al. .................. 546/340

OTHER PUBLICATIONS

Cram et al., Organic Chemistry, Second Edition, pp. 57–58, McGraw-Hill Publishers (1964).

*Primary Examiner*—Alan L. Rotman
*Attorney, Agent, or Firm*—Reed F. Riley; William H. Magidson; Ralph C. Medhurst

[57] ABSTRACT

A regiospecific, catalyzed process for preparing acyl derivatives of aromatic nitrogen-containing heterocyclic compounds in which the keto group is selectively added ortho to the nitrogen atom on the aromatic ring. In the presence of a ruthenium carbonyl compound, carbon monoxide and an olefin, the aromatic heterocyclic compound which has an unsubstituted carbon atom ortho to at least one of the heterocyclic atoms adds the acyl group essentially completely in ortho position.

7 Claims, No Drawings

REGIOSPECIFIC CARBONYLATION PROCESS FOR MAKING ACYL COMPOUNDS FROM AROMATIC HETEROCYCLES AND OLEFINS

BACKGROUND OF THE INVENTION

This application is a CIP of U.S. Ser. No. 170,839 filed Mar. 21, 1988 now abandoned.

This invention relates to a regiospecific carbonylation process for making acyl compounds from aromatic heterocyclic compounds, and, more particularly, to a catalyzed carbonylation process for the regiospecific preparation of ortho-substituted acyl compounds by reacting an aromatic sulfur or nitrogen heterocycle in the presence of an olefin.

Functionalized aromatic compounds, including aromatic heterocyclic compounds, are key intermediates in many areas of industrial organic chemistry and have substantial uses of their own in a variety of fields. Many of such materials are typically prepared by gas-phase alkylation of such substances as benzene, toluene or xylene using sieve catalysts or in the liquid phase by the more conventional Friedel-Crafts alkylation technology. Whereas many alkyl-substituted aromatics are readily prepared in the gas phase using molecular sieve catalysts, heterocyclic compounds are either difficult to functionalize using this method or the reactions are not regiospecific. Although regiospecific methods exist for alkylating or acylating this type of compound, existing techniques involve expensive materials such as lithium metal and/or are difficult to carry out on a large scale. Other less difficult and/or expensive methods of preparation such as radicalbased processes are not regiospecific and give mixtures of isomers. See, for example, U.S. Pat. Nos. 4,376,860; 4,098,908; 3,979,400; and 3,840,507.

Several papers reporting on the interaction of N-heterocyclics with $Ru_3(CO)_{12}$ have been published recently. In J. Organometallic Chem. 314, 311–22 (1986), pyridine, 2,2'-bipyridyl, pyrazole, 3,5-dimethylpyrazole and its perfluorinated derivative have been shown to react with triruthenium dodecacarbonyl to form isolatable solids. In the case of pyridine and 2,2'-bipyridyl, the compounds react to displace carbon monoxide and form a N-Ru bond. A C-Ru bond is formed also by inserting one of the cluster Ru atoms into a C—H bond ortho to the heterocyclic atom. Described in Organometallics 5, 2193-8 (1986) is the reaction with triruthenium dodecacarbonyl of quinoline, 1,2,3,4-tetrahydroquinoline, phenanthradine and 9,10-dihydrophenanthradine where similar complexes are obtained.

Now it has been found that one class of acyl compounds, ortho-substituted ketones of aromatic, nitrogen-containing heterocyclics, can be formed cheaply and highly regioselectively by catalytically carbonylating a combination of an aromatic nitrogen heterocycle and an olefin in the presence of a ruthenium carbonyl compound. This reaction appears quite general and only requires that the aromatic, nitrogen-containing heterocycle contain an unsubstituted carbon atom ortho to the ring nitrogen atom. Such compounds as 2-pyridyl ethyl ketone can be formed with close to 100% selectivity to the o-substituted isomer, which materials have substantial uses in the pharmaceutical, agricultural, and plating fields and as inhibitors for plastics.

SUMMARY OF THE INVENTION

A catalyzed regioselective process comprising combining under carbonylation conditions a nitrogen-containing aromatic heterocyclic compound and an olefin with carbon monoxide in the presence of a ruthenium carbonyl compound to selectively form an organic acyl compound in which the carbonyl group is ortho to the heterocyclic nitrogen atom.

DETAILED DESCRIPTION OF THE INVENTION

Aromatic heterocyclic compounds useful in the present invention include nitrogen heterocycles having one or more aromatic rings and containing one or more nitrogen atoms present in an aromatic ring. The ring or rings may be substituted by alkyl or aryl groups, more preferably, by $C_1$ to $C_4$ alkyl groups, but one unsubstituted carbon atom ortho to the heterocyclic atom must exist. It is believed that halo, alcohol, aldehyde and the like, substitution on the heterocyclic compound reduces the potential for the regioselective carbonylation to occur. Preferred are such N-containing compounds as pyridine, $C_1$–$C_4$ alkyl-substituted pyridines, pyridazine, $C_1$ to $C_4$ alkyl-substituted pyridazines, quinoline, $C_1$ to $C_4$ alkyl-substituted quinolines, 2,2'-bipyridyl, 1,10-phenanthroline and the like. Most preferred is pyridine or a $C_1$ to $C_4$ alkyl-substituted pyridine.

The olefin reactant can be any olefin, branched or unbranched. Diolefins such as 1,3-butadiene can be employed also, but for best results the double bonds should not be conjugated. Oligomers with terminal unsaturation are also useful in the process. Preferred are alkyl or aryl substituted $C_2$ to about $C_{30}$ olefins and oligomers having terminal unsaturation such as polypropenes and polybutenes. Some examples of useful compounds are ethylene, propylene, phenylethylene, styrene, 1-hexene, 2-hexene, isobutylene, 1,6-hexadiene, and the like.

The catalyst which is a ruthenium compound can be any ruthenium carbonyl compound. More preferred is the use of a neutrally charged ruthenium carbonyl, such as $Ru(CO)_5$, $Ru_2(CO)_9$ and $Ru_3(CO)_{12}$, and the like, and most preferred is the use of triruthenium dodecacarbonyl, $Ru_3(CO)_{12}$.

In general, the olefin is used in up to equimolar amount with the aromatic heterocyclic compound. The aromatic heterocycle can, however, be used in substantial excess and excess heterocyclic compound used as the solvent. An inert solvent such as a linear or branched hydrocarbon, e.g., hexane, or an aromatic compound such as benzene or toluene may be used with or without the use of excess heterocycle.

The catalyst which is a ruthenium carbonyl compound is generally used in small catalytic amounts. Such catalyst amounts are generally in the range of about 0.01 to about 1 weight percent of the amount of heterocycle used. As ruthenium is expensive it is expedient to use as little catalyst as possible. Since the carbonylation is believed homogeneous, it is preferred that the carbonyl catalyst be unsupported. However, a heterogeneous carbonylation with a supported ruthenium carbonyl catalyst could be desirable if the carbonyl catalyst could be fixed firmly to a support such as silica, alumina or silica alumina.

Although air should be rigorously excluded from these reactions for best results by using an inert gas or better carbon monoxide, it is not necessary to exclude water. Small amounts of water can be tolerated in the reaction systems without a significant deleterious effect.

The catalyst taught herein is highly selective and efficient, and turnover rates (mols product per mol catalyst per hour) of over 200 have been observed for the carbonylation reaction, and higher values are to be expected if the carbonylation is done on a larger scale.

In the carbonylation process taught here, the basic components are a heterocrylic compound containing at least one unsubstituted carbon atom in a position ortho to the heterocylic nitrogen atom, an olefin, a ruthenium carbonyl compound and carbon monoxide. Because addition of the olefin to the heterocylic compound through the carbonyl group can occur at either unsaturated carbon atom leading to a mixture of isomers (an alpha-olefins adds primarily at the alpha carbon), the product of the inventive process can contain two isomers. However, the process is essentially 100 percent regiospecific to ortho substitution.

The catalyzed carbonylation reaction is desirably carried out batchwise in a pressurized reactor or in a continuous stirred-tank reactor, although an ebullated, slurry or fluidized bed or other type of reaction could be useful if the reaction could be made heterogeneous as can be understood by one skilled in the art.

The carbonylation is desirably carried out in the temperature range from about 50C. to about 250C., more preferably, between about 100C. and about 200C. Although the reaction can be carried out at atmospheric pressure, elevated pressure from about 10 psig to about 1000 psig is preferable. More preferably, carbonylation is accomplished in the pressure range from about 50 psig to about 700 psig.

The following Examples will serve to illustrate certain embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

General

All heteroaromatic compounds were dried over calcium hydride and distilled before use. Liquid olefins were deoxygenated by bubbling argon through them. All carbonylations were run in a 316 stainless steel autoclave. Products were identified by gas chromatography/mass spectrometry and nuclear magnetic resonance spectroscopy.

EXAMPLE 1

A 300 mL autoclave was charged with 150 mg (0.235 mmol) of $Ru_3(CO)_{12}$ and evacuated. Dry pyridine (80 mL, 78 g, 1.0 mol) was added under vacuum and the reactor brought to 10-20 psi with nitrogen. The solution was stirred and heated to 150C. at which time 180 psi carbon monoxide was added followed by 25 mL (16.8 g, 0.2 mol) of 1-hexene. After twelve hours total run time, 61% of the 1-hexene had been converted to ketone products. Only 2-pyridyl-n-heptylketone (93%) and 2-pyridyl-1-methylhexylketone (7%) were observed as products, indicating that selectivity to o-substituted ketones was 100%. The two ortho-substituted ketones were isolated by distillation under vacuum after removal of unreacted starting materials. The mixture may be further separated, if desired, into the n-heptyl and 1-methyl hexyl compounds by fractionation if desired.

EXAMPLE 2

A 300 mL autoclave was charged with 150 mg (0.235 mmol) of $Ru_3(CO)_{12}$ and evacuated. Dry pyridine (50 mL, 48.9 g, 0.62 mol) was added under vacuum and the reactor brought to 10-20 psi with nitrogen. The solution was stirred and heated to at which time 180 psi carbon monoxide was added followed by 50 mL (33.6g, 0.4 mol) of 1-hexene. After twelve hours total run time, 46% of the 1-hexene had been converted to ketone products. Selectivity to o-substituted ketones was 100%.

EXAMPLE 3

A 300 mL autoclave was charged with 125 mg (0.197 mmol) of $Ru_3(CO)_{12}$ and evacuated. A solution of a 50/50 mixture of $C_{18}$ and $C_{20}$ alpha-olefin (25 mL, 20 g, 0.075 mol) in 80 mL (78 g, 1.0 mol) of dry pyridine was added under vacuum and the reactor brought to 10-20 psi with nitrogen. The solution was stirred and heated to 150C. at which time 200 psi carbon monoxide was added. After twelve hours total run time, 43% of the starting olefin mixture had been converted to ketone products. The solution was passed over a plug of silica gel to remove catalyst and the products isolated by distillation. Selectivity to o-substituted ketones was 100%.

EXAMPLE 4

A 300 mL autoclave was charged with 200 mg (0.315 mmol) of $Ru_3(CO)_{12}$ and evacuated. A solution of 1-hexene (25 mL, 16.8 g, 0.2 moles) in 80 mL (76.6 g, 0.82 mol) 4-picoline was added under vacuum and the reactor brought to 10-20 psi with nitrogen. The solution was stirred and heated to 150C. at which time 200 psi carbon monoxide was added. After twelve hours total run time, 51% of the starting olefin mixture had been converted to ketone products. Selectivity to o-substituted ketones was 100%.

What is claimed is:

1. A catalyzed regioselective process comprising combining under carbonylation conditions a nitrogen-containing aromatic heterocyclic compound having one to three aromatic rings and containing one or more nitrogen atoms, which ring or rings optionally substituted by alkyl or aryl groups and containing an unsubstituted carbon atom ortho to at least one of said nitrogen atoms, an olefin, and carbon monoxide in the presence of a ruthenium carbonyl compound to selectively form an organic acyl compound in which the carbonyl group is ortho to the heterocyclic nitrogen atom.

2. The process of claim 1 wherein said ruthenium carbonyl compound contains only ruthenium and carbon monoxide groups.

3. The process of claim 1 wherein said ruthenium carbonyl is $Ru_3(CO)_{12}$.

4. The process of claim 3 wherein said aromatic heterocyclic compound is a nitrogen compound, or an alkyl- or aryl-substituted nitrogen compound, containing a five- or six-membered ring, which ring contains one or two nitrogen atoms.

5. The process of claim 4 wherein said olefin is a $C_2$ to $C_{30}$ olefin.

6. The process of claim 4 wherein said aromatic heterocyclic compound is selected from the group consisting of pyridine, pyridazine, 2,2'-bipyridyl, pyrazine, quinoline, 1,10-phenanthroline, and their $C_1$ to $C_4$ alkyl-substituted derivatives, and said olefin is a $C_2$ to $C_{30}$ linear mono olefin.

7. The process of claim 4 wherein said aromatic heterocyclic compound is selected from the group consisting of pyridine and $C_1$ to $C_4$ alkyl mono-substituted pyridines and said olefin is a $C_2$ to $C_{30}$ linear monoolefin.

* * * * *